United States Patent [19]

Rigg et al.

[11] Patent Number: 5,270,209
[45] Date of Patent: Dec. 14, 1993

[54] METHOD FOR DISTINGUISHING COSMETIC STICKS CONTAINING WATER

[75] Inventors: Richard T. Rigg, Springfield Garden, N.Y.; Patrick J. Dunphy, Wellingborough; Paul C. Dunnett, Willington, both of England

[73] Assignee: Elizabeth Arden Company, Division of Conopco, Inc., New York, N.Y.

[21] Appl. No.: 723,356

[22] Filed: Jun. 28, 1991

[51] Int. Cl.⁵ .................... G01N 33/18; G01N 21/81
[52] U.S. Cl. ......................... 436/39; 422/56; 422/57; 436/169; 436/41
[58] Field of Search .................... 422/56–58; 436/39, 169, 41; 424/7.1, 63–69

[56] References Cited

U.S. PATENT DOCUMENTS

| | | | |
|---|---|---|---|
| 2,214,354 | 9/1940 | Snelling | 422/56 |
| 2,249,867 | 7/1941 | Snelling | 422/56 |
| 2,643,230 | 6/1953 | Mooradian et al. | 422/56 |
| 3,881,873 | 5/1975 | Klowden | 422/56 |
| 5,096,813 | 3/1992 | Krumhar et al. | 422/56 |

FOREIGN PATENT DOCUMENTS 61-83110  4/1986  Japan .

*Primary Examiner*—Lyle A. Alexander
*Attorney, Agent, or Firm*—Milton L. Honig

[57] ABSTRACT

A method and article is provided for distinguishing cosmetic sticks, especially lipsticks, containing water from those where water is absent. The method involves applying a test stick to a test paper or fabric impregnated with an indicator compound capable of changing color, forming a smear of the stick thereon and observing any change in color around an area of the smear.

9 Claims, No Drawings

METHOD FOR DISTINGUISHING COSMETIC STICKS CONTAINING WATER

BACKGROUND OF THE INVENTION

1. Field of the Invention

The invention concerns a method and article that provides a test for distinguishing cosmetic sticks containing water.

2. The Related Art

Cosmetic sticks require stiffening agents to render them hard. Waxes are classic stiffening agents, especially in lipsticks. As a consequence of being hydrophobic, wax formulations generally exclude water as a co-ingredient. For instance, most commercial lipsticks are devoid of any water.

Recent advances in cosmetic stick emulsification chemistry has achieved lipsticks incorporating water in amounts up to about 25%. See for instance a co-pending application Ser. No. 558,140, filed Jul. 25, 1990 (Dunphy et al). Incorporation of water into a lipstick has also been proposed in JP-A-61/83110 (Konuki) which provides for water-soluble substances to be compounded within an aqueous phase of the stick, this phase being homogeneously and stably dispersed within the waxy hydrophobic phase.

Certain problems arise with this relatively new technology. Water has a tendency to evaporate from the product, especially under conditions of prolonged storage at relatively elevated temperatures. A test would be desirable to evaluate this loss of moisture.

Another problem of the new moisture-containing lipstick technology is that a method would be desirable for demonstrating differences between traditional hydrophobic sticks and those incorporating moisture. A simple point-of-sale demonstration technique would be quite helpful in distinguishing these commercially unusual cosmetic sticks.

Accordingly it is an object of the present invention to provide a method for distinguishing moisture-containing sticks, especially lipsticks, which is simple and inexpensive to perform.

Another object of the present invention is to provide a test article in conjunction with the test method for demonstrating distinctiveness of moisture-containing cosmetic sticks, especially lipsticks.

These and other objects of the present invention will become more readily apparent through consideration of the following summary, detailed description and example which follow.

SUMMARY OF THE INVENTION

A method is provided for distinguishing cosmetic sticks containing water from those where water is absent. The method comprises applying a test cosmetic stick against a test substrate impregnated with an indicator compound, forming a smear of the cosmetic stick thereon and observing any change in color within an area of the smear.

An article is also provided for distinguishing cosmetic sticks containing moisture. The article comprises a test substrate impregnated with an indicator compound and a smear of the test cosmetic stick on the substrate, the indicator compound having caused a color change within an area of the smear.

DETAILED DESCRIPTION

Now it has been found that moisture-containing cosmetic sticks, especially lipsticks, can be distinguished by applying a streak or smear of the stick onto a special test substrate that changes color in response to the aqueous phase of the stick. Color change may arise from a pH interaction or from a change in hydration characteristics.

Anhydrous inorganic salts may give rise to color changes upon hydration. For instance, anhydrous copper sulphate or cobalt chloride may be employed as chemical indicators which can turn blue upon being hydrated.

More advantageously, the indicator can function through changes in pH. Sticks which have no moisture will not be capable of any pH interaction. Those products containing moisture may further include inorganic or organic salts which impart a particular pH to the aqueous phase.

There are two major criteria in selecting the best test substrate/indicator for the present invention. Firstly, the indicator should provide a strong color change in the appropriate range which is not masked by the native color of the cosmetic stick. Secondly, the substrate should not react in any way with the indicator.

With respect to the first criteria, when the cosmetic stick is a lipstick there arises the problem of distinguishing between pigment colors and the indicator color change. Since most pigments for lipsticks are of yellow, orange, pink and red shades, it is highly desirable to utilize an indicator dye that, upon contact with the lipstick, will change to blue or violet. Thus, it is advantageous to employ indicators such as Methyl Violet, Bromphenol Blue, Bromocresol Green, Bromthymol Blue, Thymol Blue and Thymolphthalein. Particularly preferred is Bromphenol Blue.

With respect to the second criteria, it has been found useful to employ acid treated paper when utilizing an indicator such as Bromphenol Blue that has an acid pH range, (i.e. 3.0 to 4.6). Better quality papers have an alkaline pH and would, therefore, themselves cause a color change with the indicator prior to any application of the cosmetic stick. Alkalinity arises from ordinary paper being chlorine bleached to whiten and so contains alkali residues. These types of papers, however, can be reacidified and are commercially available such as in the form of filter papers, e.g. Whatman grades No. 42 or 542, each having low ash content.

Advantageously the cosmetic stick will have an aqueous phase exhibiting a pH value which is outside of a pH range of the indicator compound. This differential between the pH value on the one hand and the pH range on the other will cause an immediate color change of the indicator held on the test substrate. A list of typical acid-based indicators may be found under Table I.

TABLE I

| | Acid-Base Indicators | | | | |
|---|---|---|---|---|---|
| Common name | Chemical name | pH range | $pK_{In}$ | Wavelength of maximum absorbance | Color change (acid-alkaline) |
| Cresol red (acid range) | o-cresolsulfonphthalein | 0.2–1.8 | | | Red to yellow |

TABLE I-continued

Acid-Base Indicators

| Common name | Chemical name | pH range | pK$_{In}$ | Wavelength of maximum absorbance | Color change (acid-alkaline) |
|---|---|---|---|---|---|
| Methyl violet | | 0.5–1.5 | | | Yellow to blue |
| Thymol blue (acid range) | Thymolsulfonphthalein | 1.2–2.8 | 1.7 | 544 | Red to yellow |
| Methyl yellow | Dimethylaminoazobenzene | 2.8–4.0 | 3.3 | 508 | Red to yellow |
| Bromphenol blue | Tetrabromophenolsulfonphthalein | 3.0–4.6 | 3.8 | 592 | Yellow to blue |
| Methyl orange | Dimethylaminoazobenzene-sulfonic acid | 3.1–4.4 | 3.5 | 506 | Red to orange-yellow |
| Bromocresol green | Tetrabromophenol-m-cresol-sulfonphthalein | 4.0–5.6 | 4.7 | 614 | Yellow to blue |
| Methyl red | Dimethylaminoazobenzene-o-carboxylic acid | 4.2–6.2 | 5.0 | 533 | Red to yellow |
| Chlorphenol red | Dichlorosulfonphthalein | 4.8–6.4 | 6.0 | 573 | Yellow to red |
| Bromthymol blue | Dibromothymolsulfonphthalein | 6.0–7.6 | 7.1 | 617 | Yellow to blue |
| Phenol red | Phenolsulfonphthalein | 6.4–8.0 | 7.8 | 558 | Yellow to red |
| Cresol red (base range) | See above | 7.2–8.8 | 8.1 | 572 | Yellow to red |
| Thymol blue (base range) | See above | 8.0–9.6 | 8.9 | 596 | Yellow to blue |
| Phenolphthalein | | 8.0–9.8 | 9.3 | 553 | Colorless to red |
| Thymolphthalein | | 9.3–10.5 | 9.9 | 598 | Colorless to blue |
| Alizarin yellow | p-Nitroaniline azo sodium salicylate | 10.0–12.0 | 11.1 | | Yellow to violet |
| 2,4,6-Trinitrotoluene | | 12.0–14.0 | | | Colorless to orange |

Dependent upon the pH of the aqueous phase of the stick, the indicator may have a pH range lying either in the alkaline or acid region of the scale. The cosmetic stick may have any pH within the foregoing proviso of being outside the indicator range, but preferably the aqueous phase will have a pH lying between 5.0 and 6.9.

Test substrates suitable for the present invention may be any fibrous flexible substance such as paper and fabrics. When a fabric, the substance may be woven or non-woven. Illustrative fibers may be those of cellulose, polyester, rayon, rayon/polypropylene, polyester/rayon, cotton and polyester/cellulose.

Cosmetic sticks of the present invention, especially lipsticks, will include a certain amount of water in combination with oils, waxes, emulsifiers and, optionally, pigments. Water is an essential component and may range in amount anywhere from about 1 to about 95%, preferably from about 2 to about 30%, optimally between about 2 and 10% by weight. Oils are normally included in compositions of the present invention at levels from about 2 to about 97%, preferably from about 30 to 70% by weight of the composition. These oils are useful for a variety of purposes such as to impart viscosity, tackiness, drag and emollient properties. A chosen oil will normally be liquid at room temperature, (i.e. 20° C.), and can comprise a single oil or a mixture of two or more oils. Examples of suitable oils include caprylic triglycerides; capric triglycerides; isostearic triglycerides; adipic triglycerides; propylene glycol myristyl acetate; lanolin oil; polybutene; isopropyl palmitate; isopropyl myristate; diethyl sebacate; diisopropyl adipate; hexadecyl stearate; cetyl oleate; oleyl alcohol; hexadecyl alcohol; wheatgerm oil; hydrogenated vegetable oils; petrolatum; modified lanolins; branched-chain hydrocarbons, alcohols and esters; castor oil; corn oil; cottonseed oil; olive oil; palm kernel oil; rapeseed oil; safflower seed oil; jojoba oil; evening primrose oil; avocado oil; mineral oil; and volatile and non-volatile silicone oils.

An emulsifier system will normally also be present in the cosmetic sticks of the present invention. Total levels of emulsifier may range from about 0.2 to about 10% by weight. Combinations of emulsifiers may be particularly useful, for instance, combinations of phospholipids combined with fatty acid derivatives. Examples of phospholipids are those within the categories of phosphoglycerides, lysophosphoglycerides, sphingomyelins and mixtures thereof. Especially useful as a phospholipid is lecithin. Fatty acid derivative-type emulsifiers may be of the type including monoacyl glycerol, diacyl glycerol and polyglycerol esters and combinations thereof. Especially preferred are glycerol monoalkanoates, an example of which are the monoglycerides of sunflower seed oil and of palm oil.

Waxes may optionally be present in amounts ranging from about 1 to about 25%, preferably from about 5 to 20% by weight. Examples of waxes include candelilla wax, ozokerite wax, carnauba wax, beeswax, spermaceti, cetyl alcohol and stearyl alcohol. Pigments are here defined as including both inorganic compounds and organic dyes which may be present in amounts from about 0.5 to about 15%, preferably from about 2 to 10% by weight. Examples of pigments include inorganic salts such as bismuth oxychloride, iron oxide, titanium dioxide and mica. Organic dyes which may serve as pigments include Blue 1 Aluminum Lakes, Red 6 Barium Lakes, Red 7 Calcium Lakes, Red 21 Aluminum Lakes, Red 27 Aluminum Lakes, Red 27 Zirconium Lakes, Yellow 5 Aluminum Lakes, Yellow 6 Aluminum Lakes, Carmine, Manganese Violet, Orange 5, Red 21, Red 27, Red 36 and mixtures thereof.

Skin active ingredients in the form of both water-soluble and insoluble substances may be included within cosmetic sticks of this invention. These ingredients may range anywhere from about 0.0001 to about 10% by weight. Examples include zinc oxide; β-glycyrrhetic acid; camomile oil; ginko biloba extract; pyroglutamic acid, salts or esters; sodium hyaluronate; 2-hydroxyoctanoic acid; sulphur; salicylic acid; carboxymethyl cysteine and mixtures thereof.

The following examples will more fully illustrate the embodiments of the present invention. All parts, percentages and proportions referred to herein and in the appended claims are by weight unless otherwise indicated.

EXAMPLE

Experiments under this Example were performed with a cosmetic emulsion lipstick containing the ingredients as listed in the Table below.

TABLE II

| Ingredient | % w/w |
|---|---|
| A. Oily Phase | |
| Oil | |
| Caprylic/capric triglyceride | 5.8 |
| Propylene glycol myristyl ether acetate | 6.0 |
| Lanolin oil | 2.5 |
| Polybutene | 0.8 |
| Caprylic/capric/isostearic/adipic triglyceride | 7.0 |
| Isopropyl palmitate | 11.6 |
| Wax | |
| Candelilla wax | 6.6 |
| Ozokerite wax | 2.5 |
| Carnauba wax | 0.4 |
| Beeswax | 4.1 |
| Lanolin | 7.0 |
| Emulsifer System | |
| Phospholipid, (soybean lecithin) | 1.0 |
| Monoglyceride | 3.5 |
| B. Aqueous Phase | |
| Glycerol | 5.0 |
| Water | 5.0 |
| Sodium hyaluronate solution | 1.0 |
| Sodium PCA solution | 2.0 |
| C. Pigments Dispersed in Castor Oil | |
| Titanium dioxide | 4.7 |
| Colorants | 7.0 |
| Castor oil | 19.5 |

The above formulation was determined to have an aqueous phase with a pH of about 6.3.

The following indicators impregnated onto Whatman filter papers were studied as listed below:

| Indicator | Solvent System |
|---|---|
| Copper Sulphate (anhydrous) | 0.1% in methanol/ethanol (1:1) |
| Cobalt Chloride (anhydrous) | 0.1% in methanol/ethanol (1:1) |
| Malachite Green | 0.1% in 95% ethanol |
| Bromocresol Green | 0.1% in 96% ethanol |
| BDH 4460 Indicator | Ethanol 96 ex J. Burroughs |

Kimwipes (from Kimberly Clark) were tested as a paper but were not sufficiently acid even after repeated washing with methanol and diluted hydrochloric acid. Optimum color intensity was achieved by using Bromphenol Blue at 0.1–2.0% in alcoholic solution impregnated into Whatman 42 (hardened) or Whatman 542 (ashless) filter papers. The papers were soaked for a few seconds in a solution (Ethanol 96 containing indicator), drained and then allowed to dry in a fume hood. Prior to use they were stored in a sealed plastic envelope.

In an alternative experiment, Hammermill Offset Opaque paper (60 weight) was employed as the test substrate. A solution of 1% Bromphenol Blue indicator and an acidifying amount of citric acid were dissolved in methanol/water solvent. The Hammermill paper was soaked in this acidified indicator solution and solvent evaporated. Tests with lipstick confirmed that the in situ acidified Hammermill paper was as effective as the pre-acidified Whatman 542 paper.

The test of the present invention was performed in the following manner. According to the best mode, a 1% Bromphenol Blue impregnated Whatman No. 542 filter paper was smeared with a red lipstick (aqueous-type) having the formula identified in Table II above. Both the smear and areas surrounding the smear rapidly turned blue. By contrast, a red commercial anhydrous lipstick, when smeared onto the Whatman 542 test paper, caused no color change; the smear remained red. In this manner it was quite easy to distinguish an aqueous-based lipstick from that of the anhydrous variety.

The foregoing description and example illustrate selected embodiments of the present invention. In light thereof, various modifications will be suggested to one skilled in the art, all of which are within the spirit and purview of this invention.

What is claimed is:

1. A method for distinguishing cosmetic sticks containing water from those where water is absent, said method comprising applying a test cosmetic stick against a test substrate, forming a smear of said stick thereon, observing any change in color within an area of said smear and correlating said change with water content of said cosmetic stick, said test substrate being impregnated with an indicator compound capable of changing color when contacted by said smear and water presence in said cosmetic stick being demonstrated by change to a color different from that of said smear.

2. A method according to claim 1 wherein said indicator is a dye selected from the group consisting of Methyl Violet, Bromphenol Blue, Bromocresol Green, Bromthymol Blue, Thymol Blue and Thymolphthalein.

3. A method according to claim 1 wherein said test substrate is an acid-treated paper.

4. A method according to claim 1 wherein said indicator is an organic dye.

5. A method according to claim 1 wherein said indicator is an inorganic anhydrous compound that changes color upon hydration.

6. A method according to claim 1 wherein the cosmetic sticks are lipsticks.

7. A method according to claim 1 wherein said test substrate is a fibrous flexible substance.

8. A method according to claim 7 wherein said fibrous flexible substance is selected from the group consisting of paper and fabric.

9. A method according to claim 8 wherein said fabric is a woven or non-woven fibrous web.

* * * * *